(12) United States Patent
Dondero

(10) Patent No.: US 6,490,729 B1
(45) Date of Patent: Dec. 10, 2002

(54) APPARATUS AND METHOD RELATING TO A QUICK ATTACHMENT AND RELEASE GOGGLE MOUNTING SYSTEM

(75) Inventor: John Dondero, Ketchum, ID (US)

(73) Assignee: Eye Safety Systems, Inc., Sun Valley, ID (US)

( * ) Notice: Subject to any disclaimer, the term of this patent is extended or adjusted under 35 U.S.C. 154(b) by 6 days.

(21) Appl. No.: 09/668,527

(22) Filed: Sep. 21, 2000

(51) Int. Cl.[7] ................................................ A61F 9/00
(52) U.S. Cl. ................................................ 2/10; 2/63
(58) Field of Search .............................. 2/5, 422, 424, 2/10, 6.2, 6.3, 425; 128/201.24

(56) References Cited

U.S. PATENT DOCUMENTS

| | | | | |
|---|---|---|---|---|
| 2,834,017 A | * | 5/1958 | Simpson et al. ................ | 2/10 |
| 3,808,604 A | * | 5/1974 | Rose .............................. | 2/10 |
| 4,686,712 A | * | 8/1987 | Spiva ............................. | 2/10 |
| 4,796,308 A | * | 1/1989 | Bourgeois ..................... | 2/243 |
| 4,869,586 A | * | 9/1989 | Chung ........................ | 351/158 |
| 5,291,880 A | * | 3/1994 | Almovist et al. ...... | 128/201.22 |
| 5,341,516 A | * | 8/1994 | Keim ............................. | 2/452 |
| 5,347,655 A | * | 9/1994 | Garrett .......................... | 2/10 |
| 5,819,318 A | * | 10/1998 | Tse ............................ | 2/182.1 |
| 5,937,439 A | * | 8/1999 | Barthold et al. ............... | 2/10 |
| 5,940,891 A | * | 8/1999 | Lane ........................... | 2/426 |
| 5,966,738 A | * | 10/1999 | Wang ............................ | 2/10 |

* cited by examiner

*Primary Examiner*—Peter Nerbun
*Assistant Examiner*—Katherine Moran
(74) *Attorney, Agent, or Firm*—Graybeal Jackson Haley LLP

(57) ABSTRACT

System and methods for mounting a goggle to a helmet. The systems and methods comprise a bracket body, with a retaining post that extends in a first direction, and a mounting bracket the extends in a second direction. The mounting bracket includes a fastener for securing the brim of a helmet in a slot formed in the mounting bracket. The retaining post has a distal portion that has a portion with a greater cross section than the remainder of the retaining post. The mounting bracket extends in a second direction. A strap is provided with a first end that is attachable to a goggle and a second end with an opening therein. The opening is sized to pass interferingly over the portion of the distal portion of the retaining post with the greater cross section.

22 Claims, 2 Drawing Sheets

APPARATUS AND METHOD RELATING TO A QUICK ATTACHMENT AND RELEASE GOGGLE MOUNTING SYSTEM

TECHNICAL FIELD

The present invention relates to quickly attaching a goggle to and releasing a goggle from a helmet.

BACKGROUND

Goggles have been available in the market place for many years. Goggles can be attached to a user's headwear such as a fireman's or construction worker's helmet. Other goggles are used by sports enthusiasts such as motorcycle riders, pilots, skydivers and skiers.

For some uses, such as a prolonged activity like skiing, a goggle can be attached to and detached from the helmet at the leisure of the user. Since the user knows when a particular activity will begin, and knows that he or she will most likely wear the goggles throughout the duration of the event or activity, the need for a quickly attachable and releasable goggle is minimal.

For other uses, such as fighting fires, there is a need to quickly attach and release the goggles, often when the user is busy doing something else and has only one hand free. Some previous mounting systems have required two hands to join two mating parts together. Some other systems require the dexterity of an un-gloved hand to attach or release the goggle from the helmet. In emergency scenarios, removing one's gloves can be a waste of precious time, or dangerous if in the vicinity of sharp or burning objects. Also, a goggle is often desired as eye protection by fire fighters and rescue personnel because a face shield alone does not provide the level of eye protection required in an environment filled with smoke or airborne debris.

Therefore, there is a need for a goggle mounting system that permits quick attachment to and release of a goggle from the helmet with one hand and while wearing gloves.

SUMMARY OF THE INVENTION

The present invention provides system, and methods for quickly attaching a goggle to a helmet and releasing the goggle from the helmet. Such systems and methods are desirable in activities of uncertain duration or which may involve abrupt changes in the type of activity or physical environment, such as fire fighting and emergency rescue. The present invention is simple to use, can be used with a helmet having a face shield, and can be readily used by someone wearing gloves. It also permits quick and simple assembly during manufacture of the helmet or field retrofit. A bracket body, which is an element of the invention, is easily installed with minimum of tools and it is also readily releasable if replacement is required.

Thus one aspect of the present invention provides a bracket body, with a retaining post that extends in a first direction and a mounting bracket that extends in a second direction. The retaining post has a distal portion that has a portion with a greater cross section than the remainder of the retaining post. The invention further includes a strap with a first end that is attachable to a goggle and a second end with an opening. The opening is sized to pass interferingly over the segment, or portion, of the distal portion having the greater cross section.

In some embodiments, the opening in the second end of the strap may be resilient to allow for some distortion or stretching during the interfering passage. The opening may be a grommet attached at the second end of the strap and that grommet may be comprised of a resilient material. Alternatively, the greater cross section portion of the retaining post may be a resilient member, such as a washer attached to the retaining post.

Another embodiment provides for the retaining post to be separated in an axial direction along a portion of its length thus forming at least two fingers. When the opening in the second strap end is passed over the greater cross section portion, the fingers can flex substantially towards one another to permit passage of the opening.

In some embodiments the first direction of the retaining post and the second direction of the mounting bracket may be substantially opposite, whereas in other embodiments the angle between the two directions may be substantially less than 180 degrees.

Another aspect of the present invention provides a mounting stud rather than a mounting bracket as described above. The mounting stud provides a different means of attachment of the bracket body to a helmet as described below in the Detailed Description.

Yet another aspect of the invention provides for the first direction and the second direction as disclosed above to define an angle of substantially less than 180 degrees. Also, the retaining post and the opening in the strap are sized to allow passage over each other. The bracket body is mounted to a helmet so the angle between the first and second directions may generally dispose the retaining post somewhat upwardly and/or rearwardly relative to the front of the helmet. This permits the tension in the strap to retain the opening around the retaining post without a requirement for there to be an enlargement of the distal end that would result in interfering passage. Consequently, due to the angle as defined above, a mirror image bracket body and associated strap may be required if a symmetrical installation is preferred. An alternative to this aspect is to curve the retaining post in such a manner that when attached to a helmet the post curves upwardly and/or rearwardly relative to the front of the helmet. The net effect of a curved retaining post, in terms of securing the strap thereon, will be substantially the same as the previously described angled retaining post.

In a further aspect, the present invention provides for a bracket body, as described above, with a first snap member extending in the first direction instead of a retaining post. Additionally, a second snap member, which is capable of releasable engagement with the first snap member, may be attached to the second end of the strap.

In another aspect, the present invention provides a bracket body with first retaining means extending in a first direction for retaining a strap, and mounting means extending in a second direction for mounting the bracket body to a helmet. The strap could include means for attaching the strap to a goggle and a second retaining means for retaining the strap to the first retaining means. The first retaining means may be a retaining post and the second retaining means may be a grommet. Alternatively, the first retaining means may be a first snap member and the second retaining means may be a second snap member, wherein the first and second snap members are capable of releasable engagement.

In yet another aspect, the present invention provides for a bracket body which is mountable to the brim of a helmet. The bracket body comprises in part a retaining post with a resilient member mounted to a distal portion thereof. The bracket body also comprises a mounting bracket substantially opposite the retaining post. The mounting bracket is formed with a slot therein which defines a first and second slot wall. The slot is adapted to slidably engage the brim of a helmet between the first and second slot walls. A fastener passes through the mounting bracket and through the first slot wall so that the bracket body is secured to the helmet brim by interaction of the fastener and the second slot wall. A strap is provided having a first end, which is attachable to a goggle, and a second end with a grommet therein. The grommet has an opening which is sized to pass interferingly over the resilient member. A further embodiment of this aspect includes a resilient washer mounted to the distal portion of the retaining post.

It is another aspect of the present invention to provide only a bracket body incorporating separately or in various combinations the attributes of the bracket bodies disclosed above.

In additional aspect, the present invention provides various bracket body and strap aspects and embodiments as disclosed above in combination with a goggle.

In a further aspect, the present invention provides the various bracket body and strap aspects and embodiments as disclosed above in combination with a goggle and a helmet.

It is intended that the various aspects and of the present invention disclosed above and hereunder may be interchanged as practicable (unless expressly stated otherwise or clear from the context). These and other aspects of the present invention will become evident upon reference to the following Detailed Description and the attached drawings

DETAILED DESCRIPTION OF THE INVENTION

The present invention provides a system and method for quickly attaching a goggle to a helmet and removing a goggle from the helmet. The invention will be described principally as it applies to a type of helmet commonly worn by fire fighters and emergency rescue personnel. However, it is useable on a wide variety of helmets, preferably with a brim, but as will be discussed below, the system is adaptable to brim-less helmets as well. The invention is advantageous because it permits a user to easily and quickly secure his or her goggles to the helmet and to easily and quickly detach the goggles from the helmet, even if the user is wearing gloves or if the helmet has a face shield.

Figure 1A:
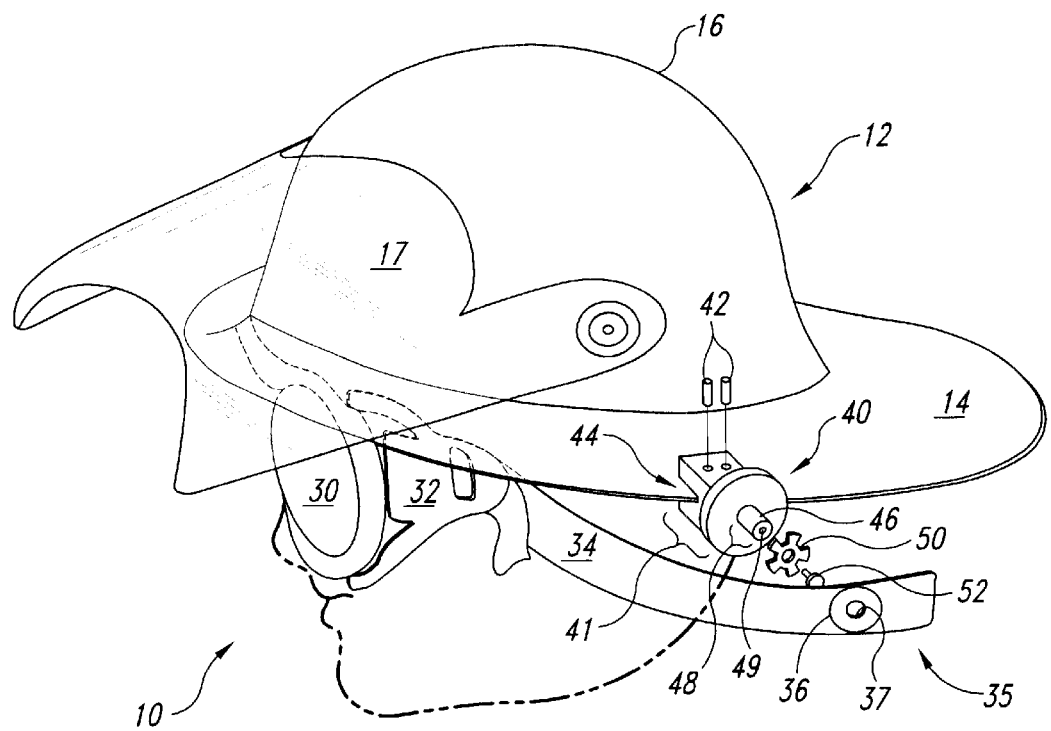
FIG. 1A is an view of the goggle mounting system in use on a firefighter's helmet, which shows in part an exploded view of a bracket body.
Figure 1B:
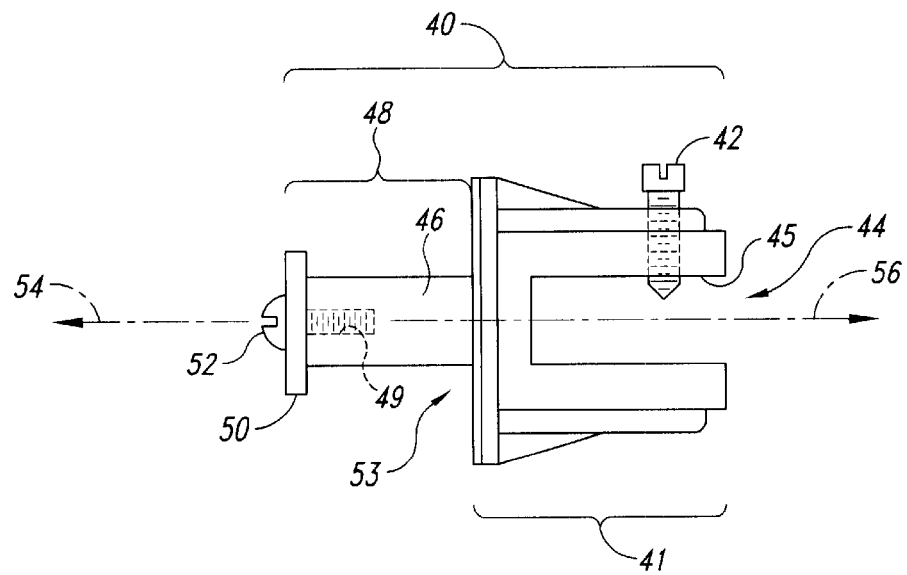
FIG. 1B is a side view of the bracket body depicted in FIG. 1A.

Referring to FIGS. 1A and 1B, FIG. 1A shows one embodiment of the present invention in use with a fireman's helmet, while FIG. 1B shows a side view of the bracket body of this embodiment shown in FIG. 1A. In FIG. 1A, a fire fighter 10 is shown wearing a helmet 12. The helmet has a brim 14 surrounding the crown 16. Mounted to the crown 16 is a face shield 17 which can be pivoted downward as desired. The fire fighter 10 is wearing a goggle 30 attached to a strap 34. The strap has a first strap end 32 that is adapted for attachment to the goggle 30. The second strap end 35 includes a grommet 36 with an opening 37. The strap 34 is attached to a bracket body 40 by passing the grommet 36 over a resilient washer 50 onto a retaining post 46. The sizes of the opening 37 and the resilient washer 50 are chosen so that there is relative interfering passage of the two elements when the goggle is attached or released.

A bracket body 40 is shown mounted to helmet brim 14. The bracket body 40 is the entire structure that is mounted to the helmet and to which the strap 34 is attached. The bracket body 40 includes a retaining post 46 which extends in a first direction 54. The first direction 54 generally points away from the helmet when the bracket body 40 is installed on the helmet brim 14. The retaining post 46 has a distal portion 48 with a hole 49 therein. By definition, the distal portion includes a portion of the retaining post 46 displaced from the base end 53 of the retaining post 46 where its base end 53 joins a mounting bracket 41. A resilient serrated washer 50 is fastened to the retaining post 46 by screw 52. The mounting bracket 41, which extends in a second direction 56, generally points towards the helmet. The mounting bracket 41 has a slot 44 establishing a first slot wall 45 and a second slot wall 43. The slot 44 receives a portion of the helmet brim 14 between the slot walls 45 and 43 and is secured to the brim by tightening set screws 42 which pass through the mounting bracket 41 and the first slot wall 45. The tightening of the set screws 42 essentially clamps the brim 14 between the set screws 42 and the second slot wall 43. An identical bracket body can be attached to the brim 14 on the other side of the helmet 12, but is not shown in this view. The bracket body 40 can be constructed of a molded plastic material. Other materials and forming methods are useful to form such a bracket such as metal machining or casting.

When a fire fighter needs to use the goggle, he simply pushes the grommet opening 37 over the resilient serrated washer 50. The grommet opening 37 and the washer 50 are sized to permit interfering passage of the washer 50 and the grommet 36. "Interfering passage" refers to the relative displacement of the washer 50 and the grommet 36, wherein the largest cross section dimension of the washer 50 is smaller than the opening 37 in the grommet 36. The dimensional differences causes there to be interference between the washer 50 and the grommet 36. However, the inherent resiliency of the washer 50 allows it to deform sufficiently to permit passage of the grommet 36.

The primary tension in the strap 34 is approximately perpendicular to the axis of the post, so it is not necessary for the strap to be fixed in place by some other means that may require greater effort, dexterity, or two hands to attach the strap 34 to the bracket body 40. When the fire fighter is ready to remove the goggle, he simply grasps the strap 34 near the grommet 36 and pulls generally outwardly or away from the brim 14; essentially in the same direction as first direction 54. There is no need for any substantial displacement of the grommet 36 perpendicular to the first direction 54. Therefore, the strap 34 can be attached or removed in a single smooth motion.

The bracket body 40 can be attached to the helmet 12 at any place along the brim 14 that suits the wearer of the helmet by simply tightening the set screws 42. As long as the retaining post 46 generally points sideways away from the helmet or somewhat rearwardly and/or upwardly the system will retain the goggle until the wearer pulls the grommet 34 off the post 46. If the bracket body 40 were mounted so that the retaining post 46 pointed somewhat towards the front of the helmet, the interference of the grommet 36 and the resilient washer 50 will still hold the grommet 36 in place unless the tension in the strap is high enough to overcome the resistance presented by the interfering fit of the grommet 36 and the resilient washer 50.

The resilient washer 50 does not need to be a washer of the serrated type shown. The resilient washer 50 may be replaced by any resilient member or device that, when incorporated as part of the bracket body, either by unitary formation or later attachment, serves the function of permitting interfering passage of the grommet 36. The resilient member may be a protrusion formed as part of the post or attached to it as by the screw 52, glue, or other method of attachment. The resilient washer, or other resilient member, establishes a portion of the retaining post 46 having a greater cross section than the remainder of the retaining post 46. This greater cross section portion, which in the case of this embodiment is resilient washer 50, need not be at the very end of retaining post 46 as shown in FIG. 1B. It could be anywhere along the length of the distal portion 48 sufficient to allow passage of the grommet 36 past it and still permit the grommet to seat along the remainder of the retaining post 46 where the cross section is approximately equal to or smaller than the size of the opening 37.

The greater cross section portion of the retaining post 46 can also be a non-resilient material or device, and the grommet of a resilient material, wherein the sizing of the respective elements still permits interfering relative passage. For example, the greater cross section portion may simply be a sphere-like shape molded on the end of the retaining post 46. The grommet can be comprised of a resilient material, such as plastic, that will stretch or deform enough to pass over the bead. In another variation, both the grommet and the greater cross section portion may be comprised of relatively resilient material so that both elements deform upon passage of the grommet over the distal portion of the retaining post. Additionally, the grommet may be replaced by a shape or device having sufficient resiliency or flexibility to deform when forced over the distal portion 48 of the retaining post 46. An alternative to the grommet shown can be as simple as a reinforced hole, much like a button hole, sewn into the second strap end 35, or a planar plastic tab mounted at the second strap end 35 that has a slit or other passage through it that will permit relative interfering passage of the greater cross section portion of the retaining post 46. In yet another variation, a hook-like structure can be mounted at the second strap 35 end that will pass around the retaining post, but is sized to not permit it to slide past the part of the retaining post including the greater cross section, namely, the distal portion. Another device that can serve the same function as a hook, is a hoop-like fastener of the type commonly use on the straps of a workman's coveralls to hook onto a button at the front of the coveralls.

Figure 2A:
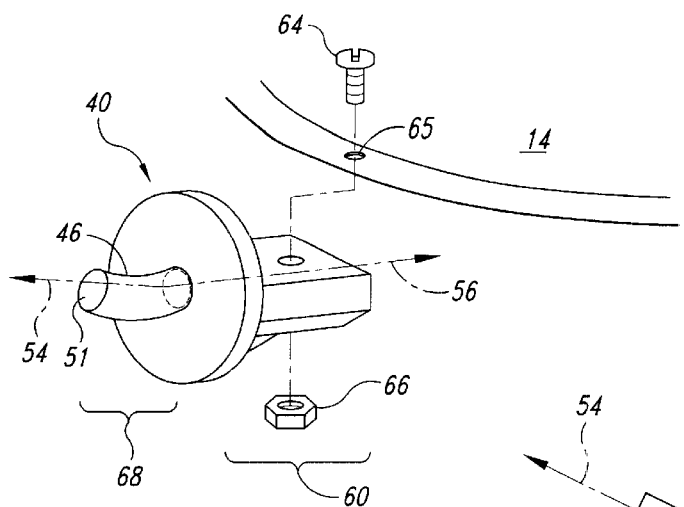
FIG. 2A. is a perspective view of an alternative embodiment of the bracket body depicting a curved retaining post and a mounting stud.
Figure 2B:
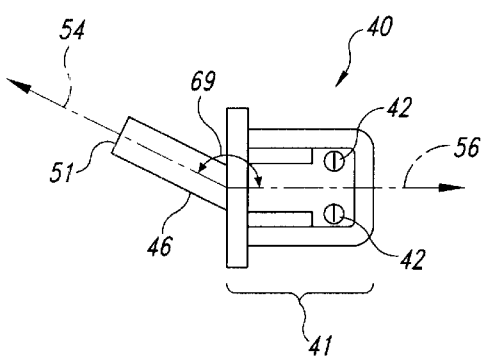
FIG. 2B is a top view of the bracket body depicted in FIG. 2A.

Referring to FIG. 2A, an alternative embodiment of the bracket body 40 is depicted. In this embodiment, the bracket body 40 does not have a mounting bracket 41 or a slot 44 as described previously. Instead, it is has a mounting stud 60 with a hole 62 through it. This configuration of bracket body 40 can be mounted to a brim by passing a fastener, such as screw 64, through an appropriately sized hole 65 in the helmet brim 14 and hole 62, then tightening nut 66 to secure the assembly. In this embodiment, as shown in FIG. 2A, the retaining post 46 can be bent or curved along a portion of its axial length 68 in a manner so that when it is attached to the brim 14, the retaining post 46 curves generally rearwardly and/or upwardly. The length of the curved portion of the retaining post 46 can vary, and it may incorporate the full length of the retaining post 46. The net effect of curving the post is to re-define the first direction 54. As indicated in FIG. 2B, the first direction 54 originates at the base 53 of the retaining post 46 and runs out through the extreme distal end 51 of the retaining post 46. Accordingly, an angle 69 is formed between the first direction 54 and the second direction 56. In this approach, having a resilient member, such as washer 50, is not necessary. The grommet opening 37 can be sized to freely pass over the distal portion 48. The strap 34 will tend to stay in place when the grommet 36 (not shown) is placed on the post, because of the tension in the strap 34, until removed by an outward force, with a nominal rearward and/or upward component, applied to the strap 34 to remove the grommet 36 from the curved retaining post 46.

As shown in FIG. 2B, an alternative to curving the retaining post is to simply set the retaining post 46 at an angle 69 that is substantially less than 180 degrees relative to the mounting bracket 41 as defined by the first direction 54, and the second direction 56, such that the retaining post 46 is disposed generally rearwards and/or upwardly (i.e., away from the direction of the tension force imparted by strap 34). (Also, note that the bracket body 40 shown in FIG. 2B includes mounting bracket 41 instead of mounting stud 60 shown in FIG. 2A. However, the two different structures for mounting the bracket body 40 to the helmet can be interchanged with the various retaining post configurations.) In this way the retaining post can achieve a generally rearward and/or upward angle and retain the strap in much the same manner as discussed previously in relation to the curved retaining post embodiment. Of course the angle between the first direction 54 and second direction 56 can be essentially equal to 180 degrees and the bracket body can be canted slightly during installation to achieve a somewhat rearward pointing retaining post to again retain the strap as just discussed. It should be noted that a single bracket body formed with an angle of less than 180 degrees between the first direction 54 and the second direction 56 would result in an asymmetrical installation unless a mirror image bracket body were formed. In other words, mirror image, or left and right hand, bracket bodies, might be used depending on the method of mounting to the helmet and any requirement that the installation be symmetrical. Likewise, depending on how the straps are adapted to attach to the goggle, there may be a requirement for mirror image straps.

Figure 3:
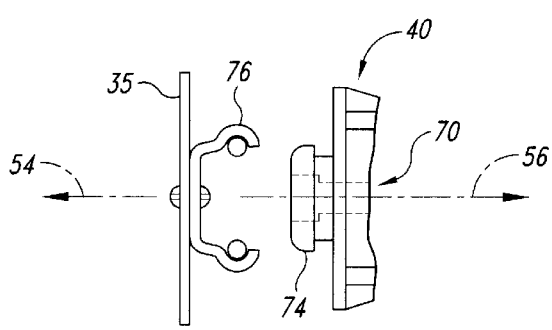
FIG. 3. is a side view of another alternative embodiment of the bracket body depicting a bracket body with a snap member thereon, the bracket body being adaptable to flush mount to the side of a helmet without a brim.

Another alternative embodiment is shown in FIG. 3. This arrangement has the advantage of being mountable to a helmet without a brim. A hole 70 through the center of bracket body 40 is used for attachment to the helmet crown 16 (helmet not shown) by a fastener such as a screw, rivet or glue. The bracket body 40 does not include a mounting bracket 41 or a mounting stud 60 as described above. Instead of employing a retaining post and grommet configuration as described above, this embodiment utilizes a first snap member 74 and a second snap member 76. First snap member 74 extends in the first direction 54 and is either attached to the bracket body 40 or formed as an integral part of the bracket body 40. The mating second snap member 76 is attached to the second strap end 35. The mating snap members can be of a variety of well known devices for accomplishing this type of function. Other mounting methods such as using mounting bracket 41 or mounting stud 60 as discussed above and shown in FIGS. 1A and 2A would work in this embodiment for use on brimmed helmets.

Figure 4:
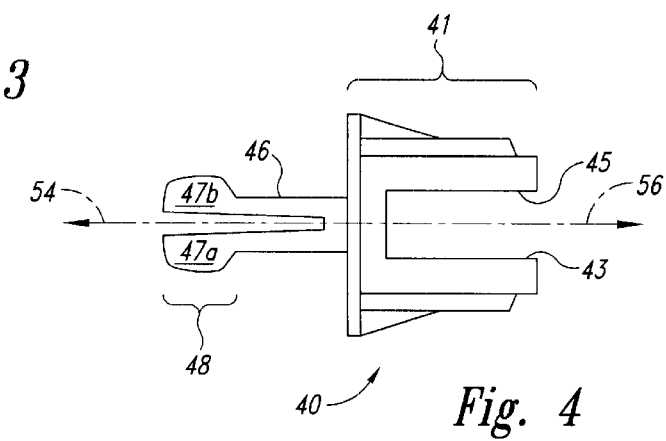
FIG. 4. is perspective view of another embodiment of the bracket body depicting a slotted retaining post with flexible fingers.

Yet another embodiment is shown in FIG. 4. In this embodiment, the retaining post 46 is separated along a portion of its length substantially parallel to its axis. Two fingers 47a and 47b are thus formed. The distal portion 48 of the retaining post 46 is sized to interfere with passage of the grommet 36 (not shown) over the distal portion 48. The fingers 47a and 47b are designed to flex substantially towards each other to the extent necessary to allow passage of the grommet 36 over the distal portion 48. Other variations of this approach are possible that might include more than two fingers.

The method of use of the systems described above is quite simple. Once the user retrieves the goggles from a storage location, such as a coat pocket or a pouch on an equipment belt, the user simply grasps either of the two straps 34 at or near the strap end 35. The user then pushes the grommet 36, or equivalent opening, past the resilient washer 50, or its equivalent structures, into a seated position on the retaining post 46. The user then grasps the other strap 34, positions the goggles over their eyes and repeats the attachment step described above. The removal of the goggles is essentially the reverse of the previous discussion. Again, as described previously, some small amount of rearward and/or upwardly force may be required in addition to an outwardly directed removal force if the retaining post is pointed rearwardly and/or upwardly to some degree. Similar forces and motions may be required if the embodiments incorporating snap members, or other hook-like or hoop-like devices, or their equivalents, are employed as described above.

It will be apparent to those skilled in the art, that the systems and methods for retaining the strap upon the retaining post and bracket mounting approaches disclosed above may be combined to create embodiments not specifically described or shown in the drawings.

The terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. The term "having" in the claims is to be interpreted as meaning the claim may include additional elements that are not specifically recited in the claim.

It is to be understood that even though various embodiments and advantages of the present invention have been set forth in the foregoing description, the above disclosure is illustrative only, and changes may be made in detail, and yet remain within the broad principles of the invention. Therefore, the present invention is to be limited only by the appended claims.

We claim:

1. A goggle mounting system for quickly mounting a goggle to and releasing a goggle from a helmet, the system comprising:
   a bracket body having a retaining post extending in a first direction, and a mounting bracket extending in a second direction, the retaining post further having a greater cross section portion at a distal portion of the retaining post; and
   a strap having a first strap end able to attach to a goggle, and a second strap end having an opening therein, the opening being sized to pass interferingly over the greater cross section portion of the retaining post.

2. The goggle mounting system of claim 1, wherein the opening is resilient.

3. The goggle mounting system of claim 1, wherein the opening is a grommet.

4. The goggle mounting system of claim 1, wherein the opening is a grommet comprised of a resilient material.

5. The goggle mounting system of claim 1, wherein the greater cross section portion of the retaining post comprises a resilient member attached to the retaining post.

6. The goggle mounting system of claim 5, wherein the resilient member is a resilient washer.

7. The goggle mounting system of claim 1, wherein the mounting bracket further comprises a slot formed therein to provide a first slot wall and a second slot wall, the slot being adapted to fit over the brim of a helmet, and a fastener passing through the mounting bracket and through the first slot wall, whereby the bracket body can be secured to a helmet brim by interaction of the fastener and the second slot wall.

8. The goggle mounting system of claim 1, wherein the first direction and the second direction are substantially opposite.

9. The goggle mounting system of claim 1, wherein the bracket body is releasable from the helmet.

10. A goggle mounting system for quickly mounting a goggle to and releasing a goggle from a helmet, the system comprising:
    a bracket body having a first retaining means for retaining a strap extending in a first direction, and a mounting means for mounting the bracket body to a helmet extending in a second direction;
    a strap having a first strap end having means for attaching to a goggle and a second strap end having a second retaining means for retaining the strap to the first retaining means;
    wherein the first retaining means is a retaining post means and the second retaining means is a grommet means.

11. A goggle mounting system for quickly mounting a goggle to and releasing a goggle from a helmet with a brim, the system comprising:
    a bracket body able to mount to the brim of a helmet, the bracket body having a retaining post and having a resilient member mounted to a distal portion of the retaining post, the retaining post extending from the bracket body and a mounting bracket substantially opposite the retaining post with a slot therein, the slot having a first slot wall and a second slot wall, the slot adapted to slidably engage a helmet brim, wherein a fastener passes through the mounting bracket and through the first slot wall such that the bracket body can be secured to a helmet brim by interaction of the fastener and the second slot wall; and
    a strap having a first strap end able to attach a goggle, and the strap having a second strap end having a grommet therein, which is sized to pass interferingly over the resilient member.

12. A goggle system mounting bracket for attachment to a helmet, the bracket comprising:
    a bracket body having a retaining post extending In a first direction, and a mounting bracket extending In a second direction, the retaining post further having a greater cross section portion at a distal portion of the retaining post said retaining post releasably engaging a goggle strap.

13. The bracket body of claim 12, wherein the greater cross section portion of the retaining post comprises a resilient member attached to the retaining post.

14. The bracket body of claim 12, wherein the greater cross section portion of the retaining post comprises a resilient washer attached to the retaining post.

15. The bracket body of claim 12, wherein the mounting bracket further comprises a slot formed therein to provide a first slot wall and a second slot wall, the slot being adapted to fit over the brim of a helmet, and a fastener passing through the mounting bracket through the first slot wall, whereby the bracket body can be secured to a helmet brim by interaction of the fastener and the second slot wall.

16. The bracket body of claim 11, wherein the bracket body is releasable from the helmet.

17. A goggle and goggle mounting system for mounting the goggle to a helmet comprising:

a goggle;

a bracket body having a retaining post extending in a first direction, and a mounting bracket extending in a second direction, the retaining post further having a greater cross section portion at a distal portion of the retaining post; and a strap having a first strap end able to attach to the goggle, and a second strap end having an opening therein, the opening being sized to pass interferingly over the greater cross section portion of the retaining post.

18. The goggle and goggle mounting system of claim 17, wherein the mounting bracket further comprises a slot formed therein to provide a first slot wall and a second slot wall, the slot being adapted to fit over the brim of a helmet, and a fastener passing through the mounting bracket and through the first slot wall, whereby the bracket body can be secured to the helmet by interaction of the fastener and the second slot wall.

19. A helmet and goggle and goggle mounting system comprising:

a helmet;

a goggle;

a bracket body having a retaining post extending in a first direction, and a mounting bracket extending in a second direction and able to mount to the helmet, the retaining post further having a greater cross section portion at a distal portion of the retaining post; and a strap having a first strap end able to attach to the goggle, and a second strap end having an opening therein, the opening being sized to pass interferingly over the greater cross section portion of the retaining post.

20. The helmet and goggle and goggle mounting system of claim 19, wherein the helmet further comprises a brim, the mounting bracket further comprises a slot formed therein to provide a first slot wall and a second slot wall, the slot being adapted to fit over the brim of the helmet, and a fastener passing through the mounting bracket and through the first slot wall, whereby the bracket body can be secured to the helmet by interaction of the fastener and the second slot wall.

21. A goggle system mounting bracket for attachment to a helmet, the bracket comprising:

a bracket body having a retaining post extending in a first direction, and a mounting bracket extending in a second direction, the retaining post further having a greater cross section portion at a distal portion of the retaining post, wherein the greater cross section portion of the retaining post comprises a resilient washer attached to the retaining post.

22. A goggle system mounting bracket for attachment to a helmet, the bracket comprising:

a bracket body having a retaining post extending In a first direction, and a mounting bracket extending In a second direction, the retaining post further having a greater cross section portion at a distal portion of the retaining post, wherein the mounting bracket further comprises a slot formed therein to provide a first slot wall and a second slot wall, the slot being adapted to fit over the brim of a helmet, and a fastener passing through the mounting bracket through the first slot wall, whereby the bracket body can be secured to a helmet brim by interaction of the fastener and the second slot wall.

\* \* \* \* \*